United States Patent [19]

Tsukada et al.

[11] Patent Number: 5,344,545
[45] Date of Patent: Sep. 6, 1994

[54] ELECTROLYTIC SENSOR FOR MEASURING THE CONTENT OF GAS IN A FLUID

[75] Inventors: Keiji Tsukada, Katsuta; Yuji Miyahara, Hitachi; Yasuhisa Shibata, Oomiya; Yoshio Watanabe, Hitachi, all of Japan

[73] Assignee: Hitachi, Ltd., Tokyo, Japan

[21] Appl. No.: 817,653

[22] Filed: Jan. 7, 1992

[30] Foreign Application Priority Data

Jan. 21, 1991 [JP] Japan .................................. 3-005250

[51] Int. Cl.$^5$ ........................................ G01N 27/404
[52] U.S. Cl. ................................ 204/415; 204/153.17; 204/414
[58] Field of Search ................ 204/414–419, 204/153.17

[56] References Cited

U.S. PATENT DOCUMENTS

| | | | |
|---|---|---|---|
| 4,062,750 | 12/1977 | Butler | 204/415 |
| 4,225,410 | 9/1980 | Pace | 422/98 |
| 4,505,807 | 3/1985 | Yamada | 204/425 |
| 4,578,154 | 3/1986 | Kitamura et al. | 204/415 |
| 4,781,798 | 11/1988 | Gough | 204/415 |
| 4,790,925 | 12/1988 | Miller et al. | 204/415 |
| 4,797,188 | 1/1989 | Tomita | 204/416 |
| 4,824,551 | 4/1989 | Rupich | 204/415 |
| 4,842,712 | 6/1989 | Seshimoto et al. | 204/416 |
| 4,950,379 | 8/1990 | Young et al. | 204/415 |
| 5,102,525 | 4/1992 | Miyahara et al. | 204/415 |
| 5,120,420 | 6/1992 | Nankai et al. | 204/415 |
| 5,138,251 | 8/1992 | Koshiishi et al. | 204/416 |
| 5,183,550 | 2/1993 | Mattiessen | 204/415 |

FOREIGN PATENT DOCUMENTS

0284518A2  9/1988  European Pat. Off. .
3921528A1  1/1991  Fed. Rep. of Germany .

OTHER PUBLICATIONS

"Oxygen Measurement by the Electrode Method"; B. Hagiwara; pp. 11 and 12, (1977) month unavailable.
Analytical Chimica; "Effect of Anode Materials on the Character . . . Electrode"; 223, (1990) month unavailable pp. 275–280.
Sensors and Actuators B, 2 (1990) month unavailable, pp. 291–295 K. Tsukada, "An Integrated Chemical Sensor w/ Multiple Ion & Gas Sensors".

Primary Examiner—T. Tung
Attorney, Agent, or Firm—Fay, Sharpe, Beall, Fagan, Minnich & McKee

[57] ABSTRACT

A gas sensor e.g. an oxygen sensor for testing body fluids, has a laminated structure with a cavity for holding a gel or liquid electrolyte in contact with a cathode and anodes formed by deposition on layers of the structure. The cathode contacts the electrolyte cavity only at a small-volume reaction region defined e.g. in a groove which communicates with a larger, laminar volume of the cavity formed e.g. by a spacer layer having through apertures. A small gas-permeable window opposes the cathode at the reaction region. The laminar construction can be mass-produced. The enlarged electrolyte reservoir lengthens the sensor life.

16 Claims, 4 Drawing Sheets

ELECTROLYTIC SENSOR FOR MEASURING THE CONTENT OF GAS IN A FLUID

FIELD OF THE INVENTION

This invention relates to gas sensors for measuring the content of a gas in a fluid. Such sensors find particular application in measuring the partial pressure of gases such as oxygen dissolved in a liquid. A specific application is the measurement of oxygen dissolved in a body fluid such as blood.

The invention is concerned with sensors of the type which use a liquid or gel electrolyte separated from the medium to be tested by a gas-permeable layer through which the gas to be measured can pass.

BACKGROUND OF THE INVENTION

A very well known example in the prior art for measuring dissolved oxygen is the Clark electrode. See, for example, pages 11 and 12 of "Oxygen Measurement by the Electrode Method" (B Hagiwara, published by Kodansha). A gas-permeable film of PTFE is fixed over an end opening of a hollow body containing an electrolyte e.g. a phosphate buffer with KCl. A cathode comprising a platinum wire extending coaxially through a glass or epoxy rod extends through the body to the gas permeable film, the cross-section of the Pt wire at the end of the rod being exposed, polished and contacting the film. An anode, usually Ag/AgCl, also contacts the electrolyte within the body. Oxygen penetrating the PTFE film is reduced at the cathode and a current dependent on the amount of oxygen flows through a circuit connecting cathode and anode under an applied voltage, with concomitant oxidation of Ag to AgCl at the cathode.

The Clark electrode is highly reliable and has a good lifetime e.g. one year. However it is very expensive and difficult to make, since it must be machined.

DISCUSSION OF PRIOR ART

Analytica Chimica Acta, 233(1990) pages 275 to 280 proposes an $O_2$ electrode, using a gel electrolyte, which can be microfabricated so as to greatly reduce manufacturing cost. A V-shaped groove is anisotropically etched in the surface of a semiconductor substrate, and anode and cathode electrodes are deposited on its side surfaces. The groove is filled with gel electrolyte and covered with a gas-permeable membrane.

This sensor could be mass-produced, but it has not been because its reliability and lifetime have been found wholly inadequate for practical application.

A further proposal is found in "Sensors and Actuators B", 2(1990) pages 291 to 295. An $O_2$ sensor was made by depositing anode and cathode electrodes on the surface of a prepared silicon substrate at the bottom of a square-sided hole. The hole was filled with electrolyte gel and the surface of the gel covered with a gas-permeable silicone rubber layer. Once again, however, the lifetime of the sensor proved to be much too short for practical application. Enlarging the sensor to improve its lifetime results in poor sensor response.

Gas sensors using solid ceramic electrolytes have been developed and these can be mass-produced. However they require high temperature operation and therefore cannot be used in many important fields in which gel and liquid electrolyte systems are used.

SUMMARY OF THE INVENTION

An object addressed herein is to provide a new construction of gas sensor using gel or liquid electrolyte. A preferred object is to provide a structure enabling simple mass-manufacture, preferably using substantially or entirely microfabrication techniques. Another preferred aim is to provide a new sensor having an adequate lifetime for practical application while achieving adequate sensor response.

In another aspect, we seek to provide new methods for making a gas sensor; also use of the new sensor.

In a first aspect, we provide a sensor for measuring the content of a gas in a fluid, which comprises an electrolyte cavity for a liquid or gel electrolyte, a sensing electrode—e.g. a cathode—and a further or reference electrode—e.g. an anode—disposed to make electrical contact with the electrolyte in the cavity, and a gas-permeable window through which the gas to be measured can reach the sensing electrode, in which the electrolyte cavity is formed with (a) a large volume reservoir region defined between gas-impermeable regions of superimposed layers comprised in a laminated structure of the sensor, and (b) a relatively small volume reaction region which is in communication with the reservoir region, and is provided at the position of the gas-permeable window and contacted by the sensing electrode.

By this means, we have been able to make a sensor with a layered structure—and therefore a structure susceptible of mass-manufacture—which can combine a satisfactory lifetime with satisfactory response. By having gas-impermeable layer portions sandwiching a large region of the electrolyte reservoir, the gas-permeable window can be confined to a small region which preferably corresponds to an exposed small region of the sensing electrode. The available total volume of electrolyte can then be made much larger than the electrolyte volume present at the sensing region, and we have found that this leads to an improvement in the life and reliability of the sensor.

The sensing electrode and a recess defining at least part of the reaction region may be formed in one layer of the laminated structure. Further recessing of this layer may also constitute or contribute to the reservoir region of the electrolyte cavity. It is also possible to provide one or more further layers in the structure, having at least one recess contributing to or constituting this reservoir. It is thus possible to adjust the electrolyte capacity of the reservoir by thickening one or more of the recessed layers and/or providing more or fewer such layers. This enables the lifetime to be selected appropriately; the sensor may be given a stereoscopic construction using a laminated construction in plural layers. This can simplify manufacture.

The reference electrode e.g. a cathode for an oxygen sensor, is desirably formed as a layer on a substrate with only a small region exposed at the reaction region. The layer comprising this electrode may be formed on an insulating substrate with a coating film formed over the substrate and electrode. This enables a recess to be made locally through the coating film exposing the electrode to the desired degree. An insulative polymeric material may be used for the coating film, and this may be recessed by a patterning process.

In one particular aspect, the recess formed in the layer which comprises the sensing electrode communicates in the structure with a larger recess formed in one or more other layers of the sensor, the larger recess being comprised in the reservoir region.

The dispositions of the various parts of the electrolyte cavity can be adjusted for various advantageous preferred effects. The reaction region, at which the gas-permeable window and sensor electrode are present, is desirably adjacent a cavity portion of a relatively small cross-sectional area e.g. as a part of a narrow groove portion. This can reduce the tendency of detectable gas to diffuse away from the sensor electrode after entering the window, adversely affecting response.

The general disposition of the reservoir portion may be divided into two major parts which communicate by a channel along which the reaction region is disposed.

In a preferred configuration, the sensor electrode and gas-permeable window oppose one another across a narrow channel to define the reaction region, being provided on adjacent layers of the laminated structure.

In a further aspect, the gas-permeable window is provided by sandwiching a piece of gas-permeable material between two impermeable layers having registered window openings at which the gas-permeable material is positioned. This construction is more practical than the prior art method of depositing the permeable layer in solution on a pre-filled gel electrolyte. Also, the layers of the sensor can be fixed together without the electrolyte e.g. by an adhesive process using heat for bonding, and the electrolyte filled into the cavity subsequently. To this end, the electrolyte cavity is preferably provided with inlet and outlet openings for filling and/or exchanging electrolyte therein. Most preferably, the cavity has a generally elongate shape between the inlet and outlet openings to facilitate injection of electrolyte from one end without forming bubbles. For this purpose the generally laminar reservoir region preferably has straight or smoothly curved, not angular, edges.

For good response it is generally desirable as stated above that the exposed sensor electrode area be very small. In many circumstances, e.g. for an oxygen sensor where the other electrode is an anode that is gradually consumed, the anode is desirably large to ensure good lifetime. The other electrode may therefore extend over at least half and more preferably at least 80% of the laminar area of the electrolyte cavity. Indeed, it may extend substantially the full laminar area of the reservoir portion thereof. This can be achieved by having this electrode exposed at the surface of at least one of the layers facing in on the reservoir portion.

In another aspect, more particular layer arrangements are proposed. In this aspect, a sensor for measuring the content of a gas in a fluid, comprising an electrolyte cavity for a liquid or gel electrolyte, a sensing electrode disposed by a gas-permeable window at a reaction region of the electrolyte cavity, and a further or reference electrode disposed to contact electrolyte in the cavity, is characterized in that the sensing electrode and the other electrode are formed on respective impermeable substrate layers which are superimposed in a laminated structure, on either side of a main reservoir portion of the electrolyte cavity.

In particular, the sensor may be an oxygen sensor, the sensing electrode a cathode and the further electrode one or more anodes.

Having the two electrodes on separate layers of the laminated structure gives important flexibility in the relative sizes of the electrodes which is desirable to achieve good sensor lifetime. Further preferred flexibility may be achieved by pre-fabricating the gas-permeable window into a layer separate from the layer having the sensing electrode, before laminating the layers together.

In another aspect, we provide a sensor for measuring the content of a gas in a fluid, comprising
a window layer having a gas-permeable window;
a sensing electrode layer of insulating material provided with a sensing electrode, and
a further electrode layer of insulating material provided with a further electrode,
these three layers being fixed together in a laminated construction with an enclosed recess defined between them which holds a liquid or gel electrolyte, the further electrode contacting the interior of said recess and the sensing electrode and gas-permeable window contacting an electrochemical reaction region which is comprised in the recess.

The volume of the recess may be adjusted by varying the thickness and/or number of the layers defining the recess. One or more layers having one or more through-apertures can be put between the layers defining the laminar boundaries of the recess, to enlarge it.

Because of the generally laminar structure of these sensors, it is possible to form electrodes in such a way that their connecting leads can be led simply through one or more through-holes penetrating one or more of the layers, to connect to terminal portions of the electrodes. Preferably the leads extend from that side of the sensor away from the window thereof.

In a further aspect, we provide a method of making a sensor for measuring the content of a gas in a sample, characterized by providing plural layers with a sensing electrode, a further electrode and a gas-permeable window, and superimposing the layers to define an electrolyte cavity between them,
a large volume reservoir region of the electrolyte cavity being defined between gas-impermeable areas of the layers and a small volume reaction region thereof at the gas-permeable window being contacted by the sensing electrode and in communication with the reservoir region.

Through the use of layers, this process is well suited for mass-production and in particular mass-production using microfabrication techniques. Electrodes may be formed by deposition on substrate layers. Selective alignment of an exposed region of the sensing electrode with the reaction region can be achieved by forming a recess in an insulating coating formed over the electrode on a substrate layer, so as both to expose the electrode and form the reaction region.

Layer substrates may be easily-processible materials such as glass or silicon layers. In a particularly preferred construction, a plurality of the sensors can be made by forming an array of sensing electrodes, an array of other electrodes, an array of gas-permeable windows, and an array of necessary recesses for forming electrolyte cavities, in the appropriate positions on plural substrate wafers, fixing the wafers together into a laminated structure of the sensor with the arrays of the various components suitably aligned, and then sub-dividing the laminated wafers to form the individual sensors. The number of steps required to make a large number of sensors can thereby be greatly reduced.

In a further aspect, the invention provides a flow cell which has a conduit or passage for through-flow of a fluid to be tested for the content of a gas, and in which a sensor as described above is installed with the gas-permeable window thereof mounted in communication with the conduit through an opening.

Correspondingly, in a still further aspect we provide a method of measuring the content of a gas in a fluid, comprising contacting the fluid with the gas-permeable window of a sensor as described above and measuring the current conditions in a circuit connecting the electrodes thereof.

In a particularly preferred embodiment of the present invention, the gas tested for is oxygen and the sensor may be used to test body fluids such as blood.

BRIEF DESCRIPTION OF THE DRAWINGS

Embodiments of the invention are now described by way of example, with reference to the accompanying drawings in which.

DETAILED DESCRIPTION OF PREFERRED EMBODIMENTS

Figure 1:
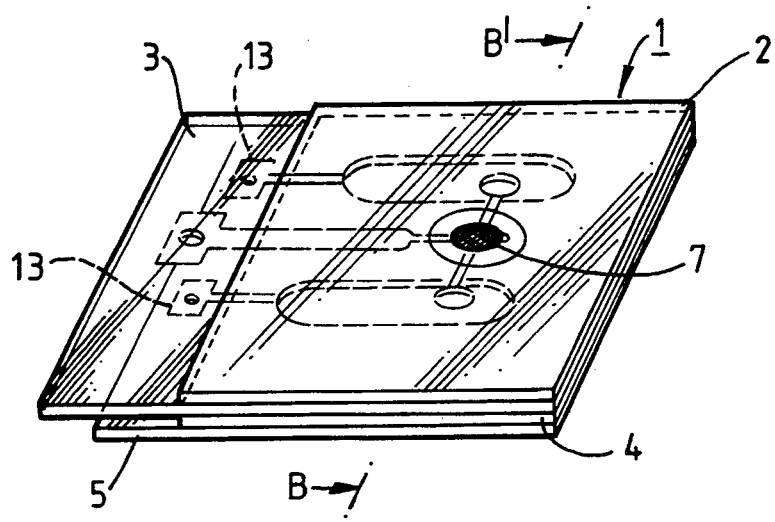
FIG. 1 is a perspective view of a laminated oxygen sensor.
Figure 2:
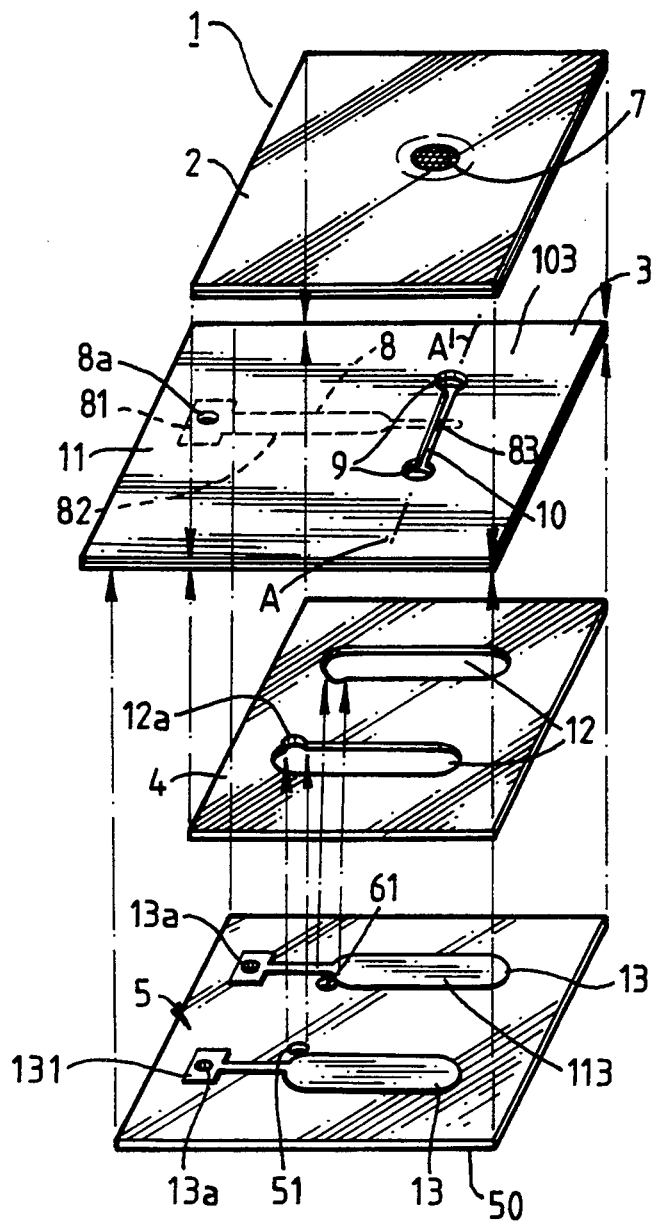
FIG. 2 is an exploded perspective view showing the parts in FIG. 1.

FIGS. 1 and 2 show a sensor for measuring the partial pressure of oxygen in e.g. blood, comprising a laminated structure 1 formed of glass layers 2,3,4,5 fixed together face-to-face by adhesive. The top layer as shown is a window layer 2 comprising a small gas-permeable sampling window 7 in an otherwise impermeable layer whose structure is described below.

The second layer is a cathode layer 3 comprising a glass substrate layer with a cathode electrode 8 formed thereon which extends beneath the gas-permeable window 7 where it is exposed by a transverse groove 10 formed in a polymeric film covering the cathode and the glass surface. Twin holes 9 penetrate the plate 3 at the ends of the groove 10.

The third layer 4 is a reservoir-forming layer having a pair of oval through-apertures 12 communicating with the through-holes 9 of the layer above. The bottom layer is an anode layer 5 having two anode electrodes 13 deposited thereon as layers to cover the bottom surface of the cavity formed in the structure by the through-apertures 12 in the layer 4 above.

The constructions of these respective layers, which can be seen in exploded view in FIG. 2, are now discussed in more detail with reference to FIGS. 3 to 5.

Figure 3:
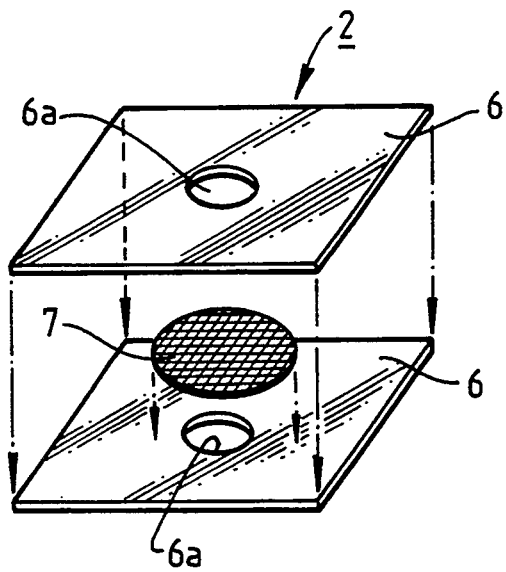
FIG. 3 is an exploded perspective view showing the construction of a layer having a gas-permeable window.

FIG. 3 shows the window layer. It is a composite formed by two thin glass sub-layers 6 sandwiching a piece of gas-permeable film material 7 in register with respective window openings 6a in each of the sub-layers 6. Gas-permeable layer 7 comprises a disc of polytetrafluoroethylene (PTFE) film of a known type and having a thickness of e.g. 15 $\mu$m. The window openings 6a are small openings e.g. 1 mm$^2$ and in this case circular, smaller in area than the film disc 7 so that it fills the resulting window as the two sub-layers are sandwiched together and bonded. Suitable bonding methods are discussed below. In this example, the layer 2 is about 10×10 mm and each sub-layer 6 is about 0.5 mm thick.

Figure 4:
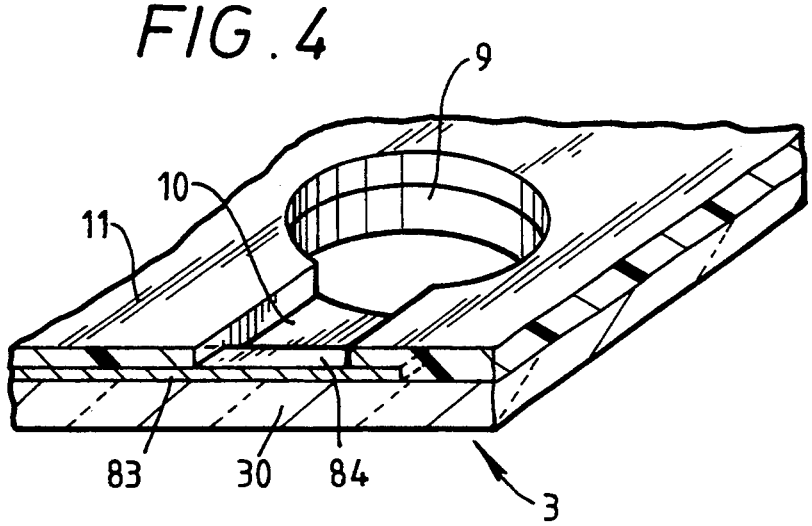
FIG. 4 is a fragmentary perspective view of a reaction region of a sensing electrode layer of the sensor section, at line A-A' in FIG. 2.

The cathode layer 3 is seen best in FIGS. 2 and 4. It comprises a glass base plate 30 of dimensions e.g. 10×15×0.5 mm, coated on its upper surface with a coating film 11 of a polymer e.g. a polyimide. A cathode electrode 8 of e.g. platinum or gold is formed on the glass base plate 30 by a suitable patterning technique e.g. a deposition technique such as sputtering, before application of the coating film. The cathode 8 extends generally lengthwise of the base plate 30 and has a wide terminal 81 at one end, an intermediate portion 82 extending most of its length, and a thin contacting portion 83 at its other end. The cathode 8 is a few $\mu$m thick. It may be deposited on a titanium underlayer to improve adhesion. The narrow contacting portion 83 is e.g. about 15 $\mu$m wide.

A pair of communication holes 9 is bored through the polyimide film 11 and glass base plate 30, symmetrically on either side of the contact portion 83 of the cathode, at about 2 mm distance. A narrow groove or channel 10 recessed into the polyimide film 11 extends between these holes 9, and is deep enough (e.g. 10 $\mu$m) to expose part of the thin end 83 of the cathode 8 where the groove 10 intersects it. The floor of groove 10 is thus formed, in part, by the very small exposed area 84 of the end of the cathode electrode. See FIG. 4. The cross-sectional area of groove 10 is very small e.g. 100 to 500 $\mu$m$^2$.

The cathode layer 3 and window layer 2 are assembled as shown with the small gas permeable window 7 lying exactly over the exposed portion 84 of the cathode. The shape and area of exposed portion 84 and gas-permeable window 7 are desirably closely matched.

Polyimide layer 11 ensures that only the relevant portion 84 of the cathode is exposed. It is also an easy material in which to form the groove 10.

Reservoir layer 4 is a single glass plate of the same square shape as window layer 2 and about 1 mm thick. The two oval cut-out portions 12 extend side-by-side longitudinally, spaced symmetrically about the cathode 8 in the layer above. Each cut-out 12 is a straight-sided oval about 6 mm long and 2 mm wide and the front end of each communicates with the respective through-hole 9 in the cathode layer 3 above when the layers are assembled together. A small part-circular recess 12a is formed in the edge of each cut-out 12 at its rear end, for reasons explained below.

The bottom layer or anode layer 5 comprises a glass base plate 50 of the same dimensions as the cathode layer base plate 30. A pair of anodes 13 is formed thereon, e.g. by deposition of a silver layer followed by chlorination to form a surface of silver chloride. Each anode 13 has an oval shape corresponding to the general outline of the cut-out recess 12 in the layer 4 above, and a rearwardly extending limb having an enlarged terminal portion 131 at the rear end thereof. A through-hole 13a is drilled through the plate 50 at each terminal portion 131. Inlet and outlet through-holes 51,61 are drilled through the plate 50 just adjacent the rear end of the said oval of each anode 13.

When the layers are assembled together, the impermeable oval areas 113 of the anode layer having the anodes 13 form a sealed floor to the oval cut-outs 12, occupying their entire area except for the small edge recesses 12a. These edge recesses 12a register respectively with the inlet and outlet openings 51,61 in the anode layer below. Corresponding impermeable areas 103 of the cathode layer 3 close off the tops of the cut-outs 12 except for their front ends which communicate with one another through the shallow groove 10 via the through-holes 9.

The four glass layers 2,3,4,5 are fixed together e.g. by a screen-printed epoxy resin adhesive, or by a low-melting point glass adhesive. In the completed construction, the cut-outs 12 form the major volume of an electrolyte cavity which is impermeably enclosed except at the inlet and outlet 51,61 and at the small gas-permeable window 7. A gel electrolyte is filled into this cavity using e.g. a syringe to force it in through the inlet 51, air escaping through the outlet 61. A corresponding procedure can be used subsequently, to exchange the electrolyte. The inlet and outlet 51,61 are then sealed with adhesive plugs.

In the resulting sensor, the major bulk of electrolyte gel is held in the cut-out reservoirs 12, with only a small volume in the groove 10. In particular, there is only a very small volume in the reaction region 112 (see FIG. 5) between the exposed portion 84 of the cathode and the gas-permeable window 7. The volume of the reaction region 112 defined between the extremities of the window 7 and exposed cathode 84 is preferably less than 5,000 $\mu m^3$; an infinitesimal percentage of the total electrolyte gel cavity volume which may be several $mm^3$.

Connecting leads 29 (shown in FIG. 7) are passed from the rear through the holes 8a,13a and bonded to the terminals 81,131 of the cathode and anodes. The leads 29 are connected into conventional oxygen sensor circuitry which need not be described.

Figure 5:
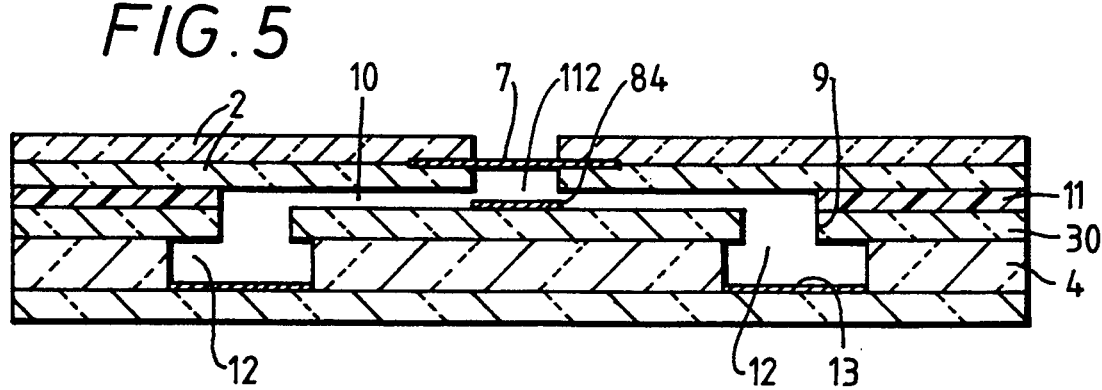
FIG. 5 is a cross-section of the assembled sensor at B-B' in FIG. 1.

FIG. 5 is a cross-section at B-B' in FIG. 1, showing (with exaggerated thickness, for clarity) the part of the sensor having the groove 10 and the reaction region 112.

Figure 6:
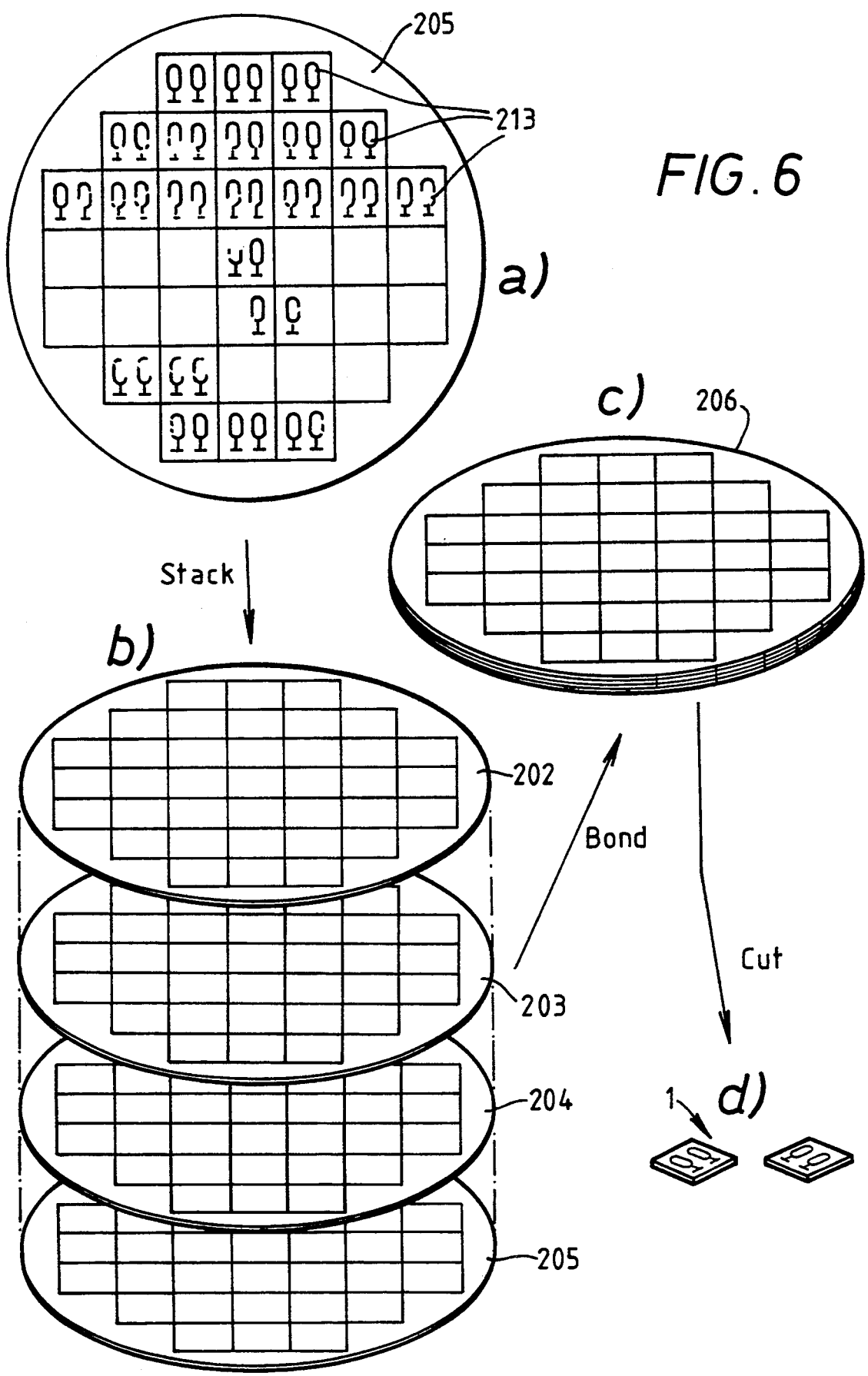
FIGS. 6a-d are a schematic illustration of preparation steps in a mass production process.

FIG. 6 illustrates schematically a mass-production technique for which the present construction is particularly suited. FIG. 6(a) shows a standard circular glass wafer 205 on which has been formed, in a regular array by standard deposition techniques, a large number of pairs of silver electrode layers 213. Each pair corresponds to the layout of electrode layers on the bottom layer 5 of a sensor as described above. Using similar known microfabrication techniques, a glass wafer 204 having an array of pairs of oval cutouts, a glass wafer 203 having an array of deposited cathodes, an overall coating film of polyimide, and an array of grooves formed therein, and a top composite wafer 202 having an array of windows with sandwiched gas-permeable film, are all formed. These are superimposed as shown schematically in FIG. 6(b) and are joined by standard bonding techniques known for glass wafers e.g. by epoxy resin or low-melting point glass adhesive. This produces a parent laminate 206 shown in FIG. 6(c) which is in effect an array of little sensors all substantially completely formed. The parent laminate 206 is then cut to form the many individual sensors 1 as indicated in FIG. 6(b). They can be filled with electrolyte before or after the cutting, but after any heating stage involved in the lamination.

Figure 7:
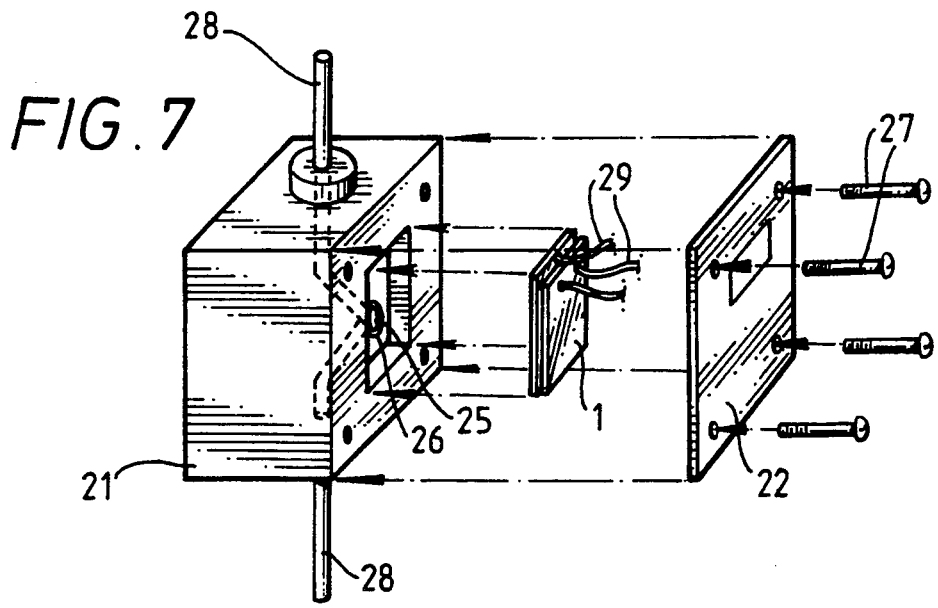
FIG. 7 shows schematically a flow cell incorporating an oxygen sensor.

FIG. 7 shows the construction of a flow cell incorporating the sensor. A small tube 28 runs through a sensor housing 21. In the housing 21, the tube 28 has a bend with an opening 25 through the tube wall, in a rectangular recess in the wall of the housing 21. A sensor 1 as described above fits into the rectangular recess and its gas-permeable window 7 is sealed against the opening 25 by an O-ring 26. A flat cover plate 22 is fastened to the housing 21 e.g. by screws 27, holding the sensor 1 into the recess. The electric leads 29 from the sensor 1 pass out through a small aperture in the cover 22.

Liquid flowing in the tube 28 is therefore exposed at the gas-permeable membrane of the sensor as it flows past the opening 25, while the O-ring 26 prevents leakage.

Gases dissolved in the flowing liquid (e.g. blood) diffuse through the gas-permeable window 7 and the oxygen content is determined in the same way as with the Clark electrode.

The following features should be noted. The groove 10 in the cathode layer 3 is sufficiently small to restrict flow of the electrolyte gel therein. Only the electrolyte gel in the reaction region 112 is involved in the electrochemical process. This gives the sensor a stable characteristic. Furthermore, the very small cross-sectional area of the groove and the small areas of exposed cathode 84 and the window 7 contribute to a sharp sensor response. Gas diffusing through the window 7 has little opportunity to diffuse away through the gel, or to reach the cathode by a long route and thereby blur the response.

However, the total capacity of electrolyte compared with the electrolyte volume at the reaction region 112 is very large, and this is an important factor for prolonging the lifetime of the sensor.

Because the electric leads 29 are let out through the back of the sensor 1, their connections can be kept away from the fluid being tested.

Because the cathode and anode electrode layers are covered, except at the portions necessary for the reaction—in particular the cathode which is covered almost entirely with the insulating film—electric leakage can be minimized.

The laminated construction is apt to be assembled using an adhesive such as a low melting-point glass, or an epoxy resin which can be screen-printed. The adhesion can therefore be done while the electrodes and other components already exist on the layers, without using damaging high temperatures.

Figure 8:
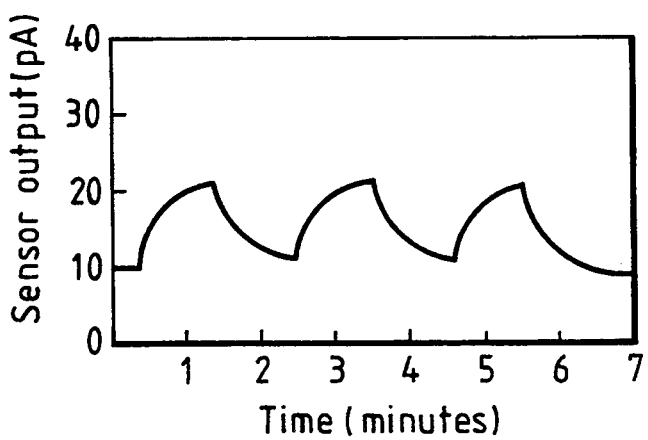
FIG. 8 shows the output response characteristic of an oxygen sensor embodying the invention.

FIG. 8 shows the response characteristics of a sensor as described above. Measurements were made by alternating first $N_2$ gas, and then $N_2$ mixed with 100 mmHg of $O_2$. A satisfactorily fast response was obtained.

Figure 9:
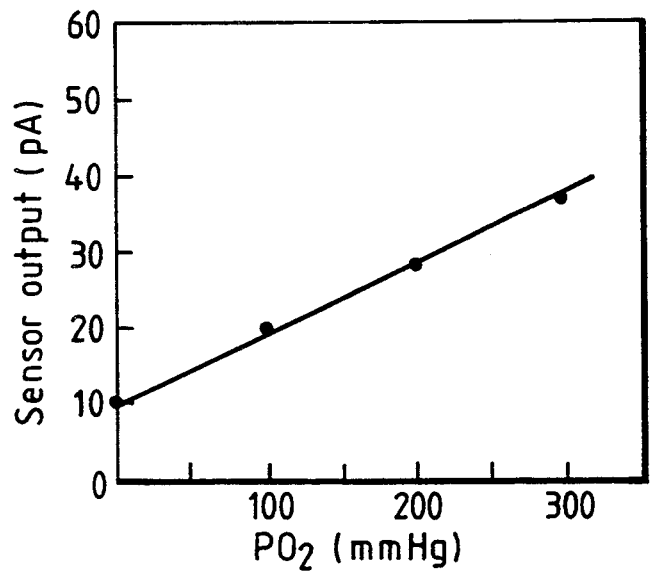
FIG. 9 shows a calibration curve of the sensor.

FIG. 9 shows the sensor output against the partial pressure of $O_2$ over a range of 0 mmHg to 300mmHg. It is seen that a satisfactory linear response was achieved. The sensitivity was 0.1 pA/mmHg.

The skilled man will understand that the particular embodiment described can be varied substantially within the teaching of the invention.

In particular, the electrolyte reservoir capacity can be adjusted. For example, the intermediate reservoir layer 4 can be omitted entirely. The reservoir volume may then be provided by the apertures 9, or by enlarged versions thereof. On the other hand, the reservoir capacity can be enlarged by adding one or more additional reservoir layers similar to layer 4, or by making that layer thicker.

We claim:

1. A sensor for measuring the content of a gas in a fluid using liquid or gel electrolyte, comprising:

a plurality of layers of impermeable material, said layers being mutually superimposed and fixed together to define a laminated structure; at least one of said layers having at least one first internal recess whereby a first electrolyte cavity is defined within the laminated structure, with a first reservoir region of said first cavity between opposed said layers of the structure; at least one other of the layers having at least one second internal recess formed by a groove that provides a second electrolyte cavity, said groove communicating with said first electrolyte cavity and having a reaction region within said second cavity that is smaller in volume than said first region and that communicates with the first region;

a gas-permeable membrane extending across a window communicating between the reaction region of the electrolyte cavity and an exterior of the sensor;

an electrolyte contained within said first and second cavities;

a sensing electrode, said sensing electrode being incorporated in the laminated structure and having an exposed portion, said exposed portion being in the reaction region and a portion of the electrolyte being held between the gas permeable membrane and the exposed portion of the sensing electrode; and a further electrode exposed to the first reservoir region.

2. A sensor as claimed in claim 1, wherein said at least one other of the layers is a sensing electrode layer comprising said sensing electrode.

3. A sensor as claimed in claim 2 in which the sensing electrode layer comprises a substrate and a coating film formed over the substrate and the sensing electrode, said second recess being formed in said coating sufficient to expose said sensing electrode.

4. A sensor as claimed in claim 2 in which said at least one of said layers is adjacent the sensing electrode layer and has said at least one first internal recess.

5. A sensor as claimed in claim 4 in which the groove is in fluid communication at at least one end thereof with at least one respective through-hole through the sensing electrode layer, said at least one through-hole being in fluid communication with said at least one first internal recess.

6. A sensor as claimed in claim 2 in which the sensing electrode layer has at least one third recess through which said groove communicates with said at least one first internal recess.

7. A sensor as claimed in claim 6 in which the sensing electrode layer has two said third recesses, at opposite ends of the groove.

8. A sensor as claimed in claim 1 in which the first region of the first electrolyte cavity is defined to have two portions connected by way of the groove.

9. A sensor as claimed in claim 1 in which the first electrolyte cavity has generally an elongate channel with opposite ends, with an electrolyte inlet and an electrolyte outlet.

10. A sensor as claimed in claim 1 in which the further electrode is laminar and the first region of the first electrolyte cavity is laminar, and the further electrode extends over at least half of the laminar area of the first region.

11. A sensor as claimed in claim 1 in which said at least one other of said layers is a sensing electrode layer comprising a substrate plate of impermeable material;

a laminar sensing electrode as said sensing electrode formed on said substrate plate, and a coating film generally covering the substrate plate and the laminar sensing electrode, wherein the groove is formed in the coating film.

12. A flow cell comprising a flow cell housing with a flow conduit having an opening; and a sensor as claimed in claim 1 mounted adjacent the conduit, with the window of the sensor communicating with the opening of the conduit.

13. A sensor for measuring the content of a gas in a fluid using a liquid or gel electrolyte, comprising:

a sensing electrode layer comprising a first substrate layer of impermeable material having a groove and a sensing electrode having an exposed portion formed on said first substrate layer in the groove, a further electrode layer comprising a second substrate layer of impermeable material and a further electrode formed on said second substrate layer, the sensing electrode layer and the further electrode layer being bonded together in superimposed relation in a laminated construction and defining therebetween an electrolyte reservoir cavity for containing an electrolyte, contacted by the further electrode, and a third substrate layer having a gas-permeable membrane extending across a window provided in the third substrate layer, the third substrate layer and the sensing electrode layer being bonded together in superimposed relation in a laminated construction so that a portion of the groove therebetween defines a reaction cavity for containing an electrolyte wherein the exposed portion of the sensing electrode is in the reaction cavity, said window communicating between an exterior of the sensor and the reaction cavity, said reaction cavity being smaller in volume than said reservoir cavity and communicating with said reservoir cavity, and said reaction cavity and said reservoir cavity containing the electrolyte with a portion thereof held between the gas permeable window and the exposed portion of the sensing electrode.

14. A sensor as claimed in claim 13, further comprising a reservoir layer, said reservoir layer having at least one through-aperture and being interposed between the sensing electrode layer and said further electrode layer so that said at least one through-aperture forms said electrolyte reservoir cavity.

15. A sensor as claimed in claim 13 in which the sensing electrode and the gas-permeable window oppose one another across the groove.

16. A laminated sensor construction comprising:

a window layer, having a first gas-impermeable substrate and a gas-permeable membrane extending across a window communicating with an exterior of the sensor in said first substrate;

a sensing electrode layer having a groove formed therein superimposed on and fixed to the window layer and having a second gas-impermeable substrate with a sensing electrode having an exposed portion that extends into a portion of the groove, wherein the groove portion forms a reaction region exposed to the gas-permeable window;

at least one reservoir layer superimposed on and fixed to the sensing electrode layer, said reservoir layer having a third gas-impermeable substrate with at least one through-aperture, and a further electrode layer having a fourth gas-impermeable substrate superimposed on and fixed on the reservoir layer, whereby opposing surfaces of the further electrode layer and the sensing electrode layer extending over the at least one through-aperture of the reservoir layer define an electrolyte reservoir cavity communicating with the reaction region through the groove formed in the sensing electrode layer, the reaction region having a smaller volume than that of said reservoir cavity, said reservoir cavity and said reaction region containing the electrolyte and holding a portion of the electrolyte in contact with the exposed portion of the sensing electrode and the gas-permeable window, and a further electrode contacting the electrolyte reservoir cavity.

* * * * *